United States Patent [19]

Yoshida et al.

[11] Patent Number: 4,804,746

[45] Date of Patent: Feb. 14, 1989

[54] ANTIBODIES TO HUMAN LEUKEMIA VIRUS-RELATED PEPTIDES AND A PROCESS FOR PRODUCTION OF THE ANTIBODIES

[75] Inventors: Mitsuaki Yoshida; Haruo Sugano, both of Tokyo; Fumio Shimizu; Kenichi Imagawa, both of Tokushima, all of Japan

[73] Assignees: Japanese Foundation for Cancer Research; Otsuka Pharmaceutical Co., Ltd., both of Japan

[21] Appl. No.: 713,659

[22] Filed: Mar. 19, 1985

Related U.S. Application Data

[62] Division of Ser. No. 535,115, Sep. 23, 1983.

[30] Foreign Application Priority Data

Jan. 7, 1983 [JP] Japan ..................................... 58-1495
Feb. 23, 1983 [JP] Japan ..................................... 58-30096

[51] Int. Cl.$^4$ ..................... C07K 15/14; A61K 39/395
[52] U.S. Cl. ..................................... 530/387; 530/806; 530/326; 530/327; 530/325; 424/89; 424/85; 424/86
[58] Field of Search ............... 530/403, 405, 406, 387, 530/363, 380, 385, 327, 326, 323, 386, 806; 424/89, 85, 86

[56] References Cited

U.S. PATENT DOCUMENTS

| | | | |
|---|---|---|---|
| 4,423,034 | 12/1983 | Nakagawa et al. | 530/405 |
| 4,438,030 | 3/1984 | Ganfield et al. | 530/387 |
| 4,525,300 | 6/1985 | Yoshida et al. | 530/806 |
| 4,572,800 | 2/1986 | Shizumi et al. | 514/2 |
| 4,599,305 | 7/1986 | Witte et al. | 530/387 |
| 4,629,783 | 12/1986 | Cosand | 435/7 |
| 4,724,258 | 2/1988 | Yoshida et al. | 530/806 |
| 4,735,896 | 4/1988 | Wang et al. | 530/812 |
| 4,743,678 | 5/1988 | Essex et al. | 530/395 |

OTHER PUBLICATIONS

Addis et al, J. Immunol., 129(5), (1982), pp. 2033-2038.
Carrel et al, Hybridoma, 2(2), 149-160, 1983 (Feb.).
Tanaka et al, Chem. Abs., 99:86304f, 1983 (Mar.).
Young et al, Chem Abs, 100:66295, 1983.
Green et al, P.N.A.S., 78(10), 6023-27, (1981).
Pesando et al, J. Immunol., 124(6), 2794-2799, (1980).

Primary Examiner—Howard E. Schain
Assistant Examiner—Jeff P. Kushan
Attorney, Agent, or Firm—Sughrue, Mion, Zinn, Macpeak and Seas

[57] ABSTRACT

An antibody of a human leukemia virus-related peptide obtained by collecting an antibody produced in a mammal body by administering to the mammal an antigen prepared by reacting a human leukemia virus-related peptide selected from the group consisting of:

(a) a peptide represented by formula (1):

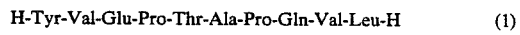

H-Tyr-Val-Glu-Pro-Thr-Ala-Pro-Gln-Val-Leu-H (1)

(b) a peptide represented by formula (2): ps R-Ile-Pro-His-Pro-Lys-Asn-Ser-Ile-Gly-Gly-Glu-Val-OH (2)

wherein R is the same as defined above;
(c) a peptide represented by formula (3):

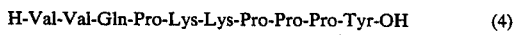

R-Thr-Trp-Thr-Pro-Lys-Asp-Lys-Thr-Lys-Val-Leu-OH (3)

wherein R is the same as defined above;
(d) a peptide represented by formula (4):

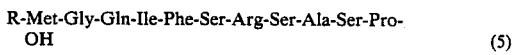

H-Val-Val-Gln-Pro-Lys-Lys-Pro-Pro-Pro-Tyr-OH (4)

(e) a peptide represented by formula (5):

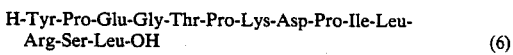

R-Met-Gly-Gln-Ile-Phe-Ser-Arg-Ser-Ala-Ser-Pro-OH (5)

wherein R is the same as defined above; and
(f) a peptide represented by formula (6):

H-Tyr-Pro-Glu-Gly-Thr-Pro-Lys-Asp-Pro-Ile-Leu-Arg-Ser-Leu-OH (6)

as a hapten, with a carrier in the presence of a hapten-carrier binding agent.

5 Claims, 3 Drawing Sheets

ANTIBODIES TO HUMAN LEUKEMIA VIRUS-RELATED PEPTIDES AND A PROCESS FOR PRODUCTION OF THE ANTIBODIES

This is a division of application Ser. No. 535,775 filed Sept. 23, 1983, now U.S. Pat. No. 4,525,300.

BACKGROUND OF THE INVENTION

1. Field of the Invention

The present invention relates to novel peptide associated with human leukemia virus (hereafter also referred to as ATLV short for adult T-cell leukemia virus or as HTLV short for human T-cell leukemia virus) and more particularly, to peptides associated with such viral infections as well as mature T-cell leukemia or lymphoma such as adult T-cell leukemia, cutaneous T-cell lymphoma, etc.

2. Development of the Invention

In the specification, amino acids, peptides, protective groups, active groups, nucleotides and others are expressed pursuant to the IUPAC Rules, the IUB Rules or common symbols established in the art when they are abbreviated; examples of which are given below. In case that optical isomers can be present with respect to amino acids or the like, an L-form is meant unless otherwise indicated.

Ser: serine
Leu: leucine
Thr: threonine
Asn: asparagine
Gln: glutamine
Glu: glutamic acid
Lys: lysine
Pro: proline
Val: valine
Trp: tryptophane
His: histidine
Asp: aspartic acid
gly: glycine
Ile: isoleucine
Ala: alanine
Tyr: tyrosine
Met: methionine
Phe: phenylalanine
Arg: arginine
Cys: cysteine
A: adenine
T: thymine
G: guanine
C: cytosine
Tos: p-toluenesulfonyl group
Boc: tert-butoxycarbonyl group
ONP: p-nitrophenoxy group
Bzl: benzyl group
OBzl: benzyloxy group
$Cl_2$-Bzl: 2,6-dichlorobenzyl group
Cl-Z: 2-chlorobenzyloxycarbonyl group Human leukemia virus has been isolated from a patient with adult T-cell leukemia (ATL) and has been shown to be closely associated with the diseases. The provirus gene integrated in host cell DNA was molecularly cloned and the complete nucleotide sequence was determined by M. Yoshida and H. Sugano, the present inventors.

The present invention has been accomplished based on the aforesaid basic information and is directed to such virus-related peptides aiming at diagnosis of such virus infections as well as a process for preparation of and a method of measurement for a specific antibody to these peptides. The nucleotide sequence coding for a precursor of core (gag) proteins of the thus determined virus gene described above is shown in Table 1 below.

TABLE 1

| ATG | GGC | CAA | ATC | TTT | TCC | CGT | AGC | GCT |
|-----|-----|-----|-----|-----|-----|-----|-----|-----|
| Met | Gly | Gln | Ile | Phe | Ser | Arg | Ser | Ala |
| AGC | CCT | ATT | CCG | CGA | CCG | CCC | CGG | GGG |
| Ser | Pro | Ile | Pro | Arg | Pro | Pro | Arg | Gly |
| CTG | GCC | GCT | CAT | CAC | TGG | CTT | AAC | TTC |
| Leu | Ala | Ala | His | His | Trp | Leu | Asn | Phe |
| CTC | CAG | GCG | GCA | TAT | CGC | CTA | GAA | CCC |
| Leu | Gln | Ala | Ala | Tyr | Arg | Leu | Glu | Pro |
| GGT | CCC | TCC | AGT | TAC | GAT | TTC | CAC | CAG |
| Gly | Pro | Ser | Ser | Tyr | Asp | Phe | His | Gln |
| TTA | AAA | AAA | TTT | CTT | AAA | ATA | GCT | TTA |
| Leu | Lys | Lys | Phe | Leu | Lys | Ile | Ala | Leu |
| GAA | ACA | CCG | GCT | CGG | ATC | TGT | CCC | ATT |
| Glu | Thr | Pro | Ala | Arg | Ile | Cys | Pro | Ile |
| AAC | TAC | TCC | CTC | CTA | GCC | AGC | CTA | CTC |
| Asn | Tyr | Ser | Leu | Leu | Ala | Ser | Leu | Leu |
| CCA | AAA | GGA | TAC | CCC | GGC | CGG | GTG | AAT |
| Pro | Lys | Gly | Tyr | Pro | Gly | Arg | Val | Asn |
| GAA | ATT | TTA | CAC | ATA | CTC | ATC | CAA | ACC |
| Glu | Ile | Leu | His | Ile | Leu | Ile | Gln | Thr |
| CAA | GCC | CAG | ATC | CCG | TCC | CGT | CCC | GCG |
| Gln | Ala | Gln | Ile | Pro | Ser | Arg | Pro | Ala |
| CCA | CCG | CCG | CCG | TCA | TCC | CCC | ACC | CAC |
| Pro | Pro | Pro | Pro | Ser | Ser | Pro | Thr | His |
| GAC | CCC | CCG | GAT | TCT | GAT | CCA | CAA | ATC |
| Asp | Pro | Pro | Asp | Ser | Asp | Pro | Gln | Ile |
| CCC | CCT | CCC | TAT | GTT | GAG | CCT | ACG | GCC |
| Pro | Pro | Pro | Tyr | Val | Glu | Pro | Thr | Ala |
| CCC | CAA | GTC | CTT | CCA | GTC | ATG | CAT | CCA |
| Pro | Gln | Val | Leu | Pro | Val | Met | His | Pro |
| CAT | GGT | GCT | CCT | CCT | AAC | CAT | CGC | CCA |
| His | Gly | Ala | Pro | Pro | Asn | His | Arg | Pro |
| TGG | CAA | ATG | AAA | GAC | CTA | CAG | GCC | ATT |
| Trp | Gln | Met | Lys | Asp | Leu | Gln | Ala | Ile |
| AAG | CAA | GAA | GTC | TCC | CAA | GCA | GCC | CCT |
| Lys | Gln | Glu | Val | Ser | Gln | Ala | Ala | Pro |

TABLE 1-continued

| | | | | | | | |
|---|---|---|---|---|---|---|---|
| GGG | AGC | CCC | CAG | TTT | ATG | CAG | ACC | ATC |
| Gly | Ser | Pro | Gln | Phe | Met | Gln | Thr | Ile |
| CGG | CTT | GCG | GTG | CAG | CAG | TTT | GAC | CCC |
| Arg | Leu | Ala | Val | Gln | Gln | Phe | Asp | Pro |
| ACT | GCC | AAA | GAC | CTC | CAA | GAC | CTC | CTG |
| Thr | Ala | Lys | Asp | Leu | Gln | Asp | Leu | Leu |
| CAG | TAC | CTT | TGC | TCC | TCC | CTC | GTG | GCT |
| Gln | Tyr | Leu | Cys | Ser | Ser | Leu | Val | Ala |
| TCC | CTC | CAT | CAC | CAG | CAG | CTA | GAT | AGC |
| Ser | Leu | His | His | Gln | Gln | Leu | Asp | Ser |
| CTT | ATA | TCA | GAG | GCC | GAA | ACC | CGA | GGT |
| Leu | Ile | Ser | Glu | Ala | Glu | Thr | Arg | Gly |
| ATT | ACA | GGT | TAT | AAC | CCA | TTA | GCC | GGT |
| Ile | Thr | Gly | Tyr | Asn | Pro | Leu | Ala | Gly |
| CCC | CTC | CGT | GTC | CAA | GCC | AAC | AAT | CCA |
| Pro | Leu | Arg | Val | Gln | Ala | Asn | Asn | Pro |
| CAA | CAA | CAA | GGA | TTA | AGG | CGA | GAA | TAC |
| Gln | Gln | Gln | Gly | Leu | Arg | Arg | Glu | Tyr |
| CAG | CAA | CTC | TGG | CTC | GCC | GCC | TTC | GCC |
| Gln | Gln | Leu | Trp | Leu | Ala | Ala | Phe | Ala |
| GCC | CTG | CCG | GGG | AGT | GCC | AAA | GAC | CCT |
| Ala | Leu | Pro | Gly | Ser | Ala | Lys | Asp | Pro |
| TCC | TGG | GCC | TCT | ATC | CTC | CAA | GGC | CTG |
| Ser | Trp | Ala | Ser | Ile | Leu | Gln | Gly | Leu |
| GAG | GAG | CCT | TAC | CAC | GCC | TTC | GTA | GAA |
| Glu | Glu | Pro | Tyr | His | Ala | Phe | Val | Glu |
| CGC | CTC | AAC | ATA | GCT | CTT | GAC | AAT | GGG |
| Arg | Leu | Asn | Ile | Ala | Leu | Asp | Asn | Gly |
| CTG | CCA | GAA | GGC | ACG | CCC | AAA | GAC | CCC |
| Leu | Pro | Glu | Gly | Thr | Pro | Lys | Asp | Pro |
| ATC | TTA | CGT | TCC | TTA | GCC | TAC | TCC | AAT |
| Ile | Leu | Arg | Ser | Leu | Ala | Tyr | Ser | Asn |
| GCA | AAC | AAA | GAA | TGC | CAA | AAA | TTA | CTA |
| Ala | Asn | Lys | Glu | Cys | Gln | Lys | Leu | Leu |
| CAG | GCC | CGA | GGA | CAC | ACT | AAT | AGC | CCT |
| Gln | Ala | Arg | Gly | His | Thr | Asn | Ser | Pro |
| CTA | GGA | GAT | ATG | TTG | CGG | GCT | TGT | CAG |
| Leu | Gly | Asp | Met | Leu | Arg | Ala | Cys | Gln |
| ACC | TGG | ACC | CCC | AAA | GAC | AAA | ACC | AAA |
| Thr | Trp | Thr | Pro | Lys | Asp | Lys | Thr | Lys |
| GTG | TTA | GTT | GTC | CAG | CCT | AAA | AAA | CCC |
| Val | Leu | Val | Val | Gln | Pro | Lys | Lys | Pro |
| CCC | CCA | AAT | CAG | CCG | TGC | TTC | CGG | TGC |
| Pro | Pro | Asn | Gln | Pro | Cys | Phe | Arg | Cys |
| GGG | AAA | GCA | GGG | CAC | TGG | AGT | CGG | GAC |
| Gly | Lys | Ala | Gly | His | Trp | Ser | Arg | Asp |
| TGC | ACT | CAG | CCT | CGT | CCC | CCC | CCC | GGG |
| Cys | Thr | Gln | Pro | Arg | Pro | Pro | Pro | Gly |
| CCA | TGC | CCC | CTA | TGT | CAA | GAC | CCA | ACT |
| Pro | Cys | Pro | Leu | Cys | Gln | Asp | Pro | Thr |
| CAC | TGG | AAG | CGA | GAC | TGC | CCC | CGC | CTA |
| His | Trp | Lys | Arg | Asp | Cys | Pro | Arg | Leu |
| AAG | CCC | ACT | ATC | CCA | GAA | CCA | GAG | CCA |
| Lys | Pro | Thr | Ile | Pro | Glu | Pro | Glu | Pro |
| GAG | GAA | GAT | GCC | CTC | CTA | TTA | GAC | CTC |
| Glu | Glu | Asp | Ala | Leu | Leu | Leu | Asp | Leu |
| CCC | GCT | GAC | ATC | CCA | CAC | CCA | AAA | AAC |
| Pro | Ala | Asp | Ile | Pro | His | Pro | Lys | Asn |
| TCC | ATA | GGG | GGG | GAG | GTT | | | |
| Ser | Ile | Gly | Gly | Glu | Val | | | |

From Table 1 above, it is shown that the precursor of core proteins is composed of 429 amino acids. In light of the structure of the terminus p-24 previously reported (*Proc. Natl. Acad. Sci., U.S.A.*, vol 79, pp. 1291–1294 (1982)), it was expected that the precursor would be further cleaved to form core proteins having the termini p-14, p-24 and p-10.

Based on the foregoing viewpoint, the present inventors have found specific peptides which can be haptens of proteins (core proteins) associated with human leukemia virus described above and have accomplished the present invention.

SUMMARY OF THE INVENTION

That is, the present invention relates to an anti-body of a human leukemia virus-related peptide obtained by collecting an antibody produced in a mammal body by administering to the mammal an antigen prepared by reacting a human leukemia virus-related peptide selected from the group consisting of:

(a) a peptide represented by formula (1):

H-Tyr-Val-Glu-Pro-Thr-Ala-Pro-Gln-Val-Leu-OH   (1)

(b) a peptide represented by general formula (2):

R-Ile-Pro-His-Pro-Lys-Asn-Ser-Ile-Gly-Gly-Glu-Val-OH   (2)

wherein R is a hydrogen atom or a group represented by the general formula H-Tyr;

(c) a peptide represented by general formula (3):

R-Thr-Trp-Thr-Pro-Lys-Asp-Lys-Thr-Lys-Val-
Leu-OH    (3)

wherein R is the same as defined above;
(d) a peptide represented by formula (4):

H-Val-Val-Gln-Pro-Lys-Lys-Pro-Pro-Pro-Tyr-OH    (4)

(e) a peptide represented by general formula (5):

R-Met-Gly-Gln-Ile-Phe-Ser-Arg-Ser-Ala-Ser-Pro-
OH    (5)

wherein R is the same as defined above; and,
(f) a peptide represented by formula (6):

H-Tyr-Pro-Glu-Gly-Thr-Pro-Lys-Asp-Pro-Ile-leu-
Arg-Ser-Leu-OH    (6)

as a haptem, with a carrier in the presence of a hapten-carrier binding agent.

The present invention further relates to a process for production of the foregoing antibody.

The present invention also relates to human leukemia virus-related peptide and a process for production thereof.

DESCRIPTION OF THE PREFERRED EMBODIMENTS

The peptides of the present invention shown by formulae (1) to (6) described above can all be easily prepared by simple operations utilizing easily accessible, commercially available amino acids. From each of the peptides, antigens can be prepared using them as haptens. From the thus obtained antigens, antibodies having a specific reactivity with virus-associated proteins can be obtained. These specific antibodies are usable for purification of virus-associated proteins, by binding these antibodies to carriers for use of, e.g., affinity chromatography, and utilizing the bound antibodies in the chromatography, etc. The specific antibodies can also be utilized as specific antibodies in various immunological measurements of such virus-associated proteins. Thus, these antibodies are useful for diagnosis of human leukemia virus infections and further for diagnosis, studies, etc. of mature T-cell leukemia or lymphoma such as adult T-cell leukemia, cutaneous T-cell lymphoma, etc. as well as diseases related thereto.

The peptides of the present invention represented by the general formulae (1) through (6) can be prepared by conventional processes for synthesizing peptides; more specifically, using processes as described in Schroder and Luhke, *The Peptides*, vol. 1 (1966), published by Academic Press, New York, U.S.A., or Izumiya et al., *Synthesis of Peptides*, (1975), published by Maruzen Publishing Co., Ltd., for example, an azide process, a chloride process, an acid anhydride process, a mixed anhydride process, a DCC process, an active ester process (a p-nitrophenyl ester process, an N-hydroxysuccinimide ester process, a cyanomethyl ester process, etc.), a process using a Woodward reagent K, a carbodiimidazole process, an oxidative reduction process, a DCC/additive (HONB, HOBt, HOSu) process, etc. Solid phase and liquid phase syntheses are both applicable to the foregoing processes.

The peptides of the present invention are prepared in accordance with the aforesaid processes for synthesizing ordinary polypeptides, generally either by a so-called stepwise process which comprises condensing an amino acid to the terminal amino acid one by one in sequence, or by coupling fragments divided into several groups to the terminal amino acid. In more detail, for example, in case that a solid phase synthesis is adopted, the C terminal amino acid is bound to an insoluble carrier through its carboxyl group. The insoluble carrier is not particularly limited as long as it has a binding capability to a reactive carboxyl group. Examples of such insoluble carriers include halogenomethyl resins such as chloromethyl resin, bromomethyl resin, etc.; hydroxymethyl resins, phenol resins, tert-alkyloxycarbonylhydrazidated resins, etc.

After the amino protective group is removed, an amino group-protected amino acid is bound in sequence in accordance with the amino acid sequence shown by general formulae (1) through (6) through condensation of its reactive amino group and the reactive carboxyl group, in sequence, to synthesize step by step. After synthesizing the complete sequence, the peptide is split off from the insoluble carrier to produce the protein.

In the foregoing process, it is preferred that respective amino acids of histidine, arginine, tyrosine, glutamic acid, threonine, lysine, aspartic acid and serine be protected at the side chain functional groups. These functional groups at the side chain are protected with ordinary protective groups which are split off after completion of the reaction. The functional groups which take part in the reaction are generally activated. These processes are known and reagents used in these processes are also appropriately chosen from known ones.

Examples of protective groups for amino groups include a benzyloxycarbonyl, Boc, tert-amyloxycarbonyl, isobornyloxycarbonyl, p-methoxybenzyloxycarbonyl, Cl-Z, adamantyloxycarbonyl, trifluoroacetyl, phthalyl, formyl, o-nitrophenylsulfenyl, diphenylphosphinothioyl group, etc.

Examples of protective groups for the imino group of histidine include a Tos, Bzl, benzyloxycarbonyl, trityl group, etc.

Examples of proective groups for arginine include a Tos, nitro, benzyloxycarbonyl group, etc.

Examples of protective groups for the hydroxy groups of serine and threonine include a Bzl, tert-butyl, acetyl, tetrahydropyranyl group, etc.

Examples of protective groups for the hydroxy group of tyrosine include a Bzl, Cl$_2$-Bzl, benzyloxycarbonyl, acetyl, Tos group, etc.

Examples of protective groups for the amino group of lysine include a benzyloxycarbonyl, Cl-Z, Cl$_2$-Bzl, Boc, Tos group, etc.

Protection for the carboxyl groups of glutamic acid and aspartic acid includes esterification of the carboxylic acids with benzyl alcohol, methanol, ethanol, tert-butanol, etc.

Examples of activated carboxyl groups include the corresponding acid chlorides, acid anhydrides or mixed acid anhydrides, azides, active esters (esters with pentachlorophenol, p-nitrophenol, N-hydroxysuccinimide, N-hydroxybenzotriazole, N-hydroxy-5-norbornene-2,3-dicarboxydiimide, etc.).

In some cases, the peptide bond forming reaction may also be carried out in the presence of carbodiimide reagents such as dicyclohexylcarbodiimide, carbodiimidazole, etc. or tetraethylpyrophosphine, etc.

Hereafter, the preparation of the peptides in accordance with the present invention will be explained more specifically with reference to reaction equations below, as an example.

(Reaction Equations 1)

A—Tyr—OH        (a)

A—Tyr—R¹        (b)

H—Tyr—R¹        (c)

A—Pro—OH        (d)

A—Pro—Tyr—R¹    (e)

A—Val—Val—Gln—Pro—Lys—Lys—Pro—Pro—Pro—Tyr—R¹   (f)

H—Val—Val—Gln—Pro—Lys—Lys—Pro—Pro—Pro—Tyr—OH   (4)

wherein A represents a protective group for an amino group and R¹ represents an insoluble carrier.

Of the foregoing, preferred examples of A include Boc, a benzyloxycarbonyl group, a p-methoxybenzyloxycarbonyl group or the like and preferred examples of R¹ include chloromethylated polystyrene or the like, respectively.

In case that amino acids used possess functional groups at the side chain thereof which do not participate in each of the reactions, the amino acids are protected by the protective groups described above in a conventional manner and the protective groups are split off at the same time as splitting-off of the insoluble carrier R¹.

In the processes described above, the reaction of the amino acid (a) with the insoluble carrier R¹ is carried out by utilizing the reactive carboxyl group of the amino acid (a) and binding it to R¹ in a conventional manner. The reaction is effected in an appropriate solvent in the presence of basic compounds, e.g., triethylamine, potassium tert-butoxide, cesium carbonate, cesium hydroxide, etc., in the case of using, e.g., chloromethylated polystyrene. Examples of solvents include dimethylformamide (DMF), dimethylsulfoxide (DMSO), pyridine, chloroform, dioxane, dichloromethane, tetrahydrofuran, N-methylpyrrolidone, hexamethylphosphoric acid triamide, etc. or a mixture solvent thereof. The above reaction is generally completed at temperatures of about 0° to about 85° C., preferably at 25° to 80° C. for several minutes to about 24 hours. It is preferred that an amount of the amino acid to the insoluble carrier be set forth such that the former is employed in an excess amount, generally 1 to 3 time equivalents per equivalent of the latter.

Splitting of the protective group A for the thus obtained amino acid shown by general formula (b) is carried out in a conventional manner. For example, there are hydrogenation using catalysts such as palladium, palladium black, etc.; a reductive method such as reduction with metallic sodium in liquid ammonia; acidolysis using strong acids such as trifluoroacetic acid, hydrogen chloride, hydrogen fluoride, methanesulfonic acid, hydrogen bromide, etc. The hydrogenation using the foregoing catalysts can be carried out, e.g., under hydrogen pressure of 1 atm at temperatures of 0° to 40° C. It is preferred that the catalyst be used generally in an amount of about 100 mg to about 1 g. The reaction is generally completed within about 1 to about 48 hours. The acidolysis described above is carried out generally at temperatures of about 0° to about 30° C., preferably 0° to 20° C. for about 15 minutes to about 1 hour, in the absence of any solvent. It is preferred that the acid be used in an amount of generally 5 to 10 times that of the raw compound. When splitting-off of the protective group A alone is desired in the acidolysis, it is preferred to use trifluoroacetic acid or hydrogen chloride as the acid. The aforesaid reduction with metallic sodium in liquid ammonia can be carried out generally at temperatures of about −40° to about −70° C., using metallic sodium in such an amount that the reaction mixture is colored to permanent blue for about 30 seconds to about 10 minutes.

The reaction of th subsequently obtained amino acid in a solid phase shown by general formula (c) and the amino acid (d) (or a derivative thereof in which the carboxyl group is activated) is carried out in the presence of a solvent. As solvents, there can be used various known solvents conventionally used in peptide condensation, for example, anhydrous dimethylformamide, dimethylsulfoxide, pyridine, chloroform, dioxane, dichloromethane, tetrahydrofuran, ethyl acetate, N-methylpyrrolidone, hexamethylphosphoric acid triamide or a solvent mixture thereof. The reaction can also be conducted, if necessary and desired, in the presence of reagents conventionally employed in ordinary peptide bond forming reactions, for example, dehydrating and condensing agents such as carbodiimides, e.g., N,N-dicyclohexylcarbodiimide (DCC), N-ethyl-N'-dimethylaminocarbodiimide, 1-ethyl-3-diisopropylaminocarbodiimide, 1-cyclohexyl-3-(2-morpholinyl-4-ethyl)carbodiimide, etc. While there is no particular limitation to the proportion of the amino acid (c) to the amino acid (d) to be used, it is preferred that the latter be employed in an amount of an equimolar amount to 10 time moles that of the former, preferably from an equimolar amount to 5 time moles. There is no particular limitation to the amount of the dehydrating and condensing agent to be used, either; the agent is generally employed preferably in an equimolar amount to that of the amino acid (d). The reaction temperature is suitably chosen from a normal range conventionally used for peptide bond forming reactions, generally from the range of about −40° to about 60° C., preferably from the range of about −20° to about 40° C. The reaction time is generally set forth for about several minutes to about 30 hours.

The thus obtained peptide shown by general formula (e) is, after splitting-off the protective group A as described above, condensed in sequence with each of the amino acids, A-Pro-OH, A-Pro-OH, A-Lys-OH, A-Lys-OH, A-Pro-OH, A-Gln-OH, A-Val-OH and A-Val-OH, in accordance with the amino acid sequence shown by general formula (4) or, derivatives thereof wherein the functional groups at the side chain are protected or the carboxyl groups are activated. Thus, the peptide shown by general formula (e) can be introduced into the peptide represented by general formula (f). These condensation and splitting-off of the protective group A are carried out in a manner similar to those described above.

Thus thus obtained peptide (f) can be introduced into the peptide shown by general formula (4) by splitting-off of the protective group A, splitting-off of the protective groups of the amino acid at the side chain thereof and removing the insoluble carrier $R^1$. Here the removal of the protective groups at the side chain functional groups and the insoluble carrier $R^1$ can be carried out in a manner similar to the splitting-off of the protective group A; in this case, it is preferred to use hydrogen fluoride or hydrogen bromide as the acid. All of the amino acids used in the aforesaid processes may be those commercially available.

The thus produced peptide of the present invention shown by formula (4) can be isolated and purified from the reaction mixture by means of peptide separation, e.g., extraction, distribution, column chromatography, etc.

Further, the peptides represented by general formulae (1) to (3), (5) and (6) can also be prepared in a manner similar to the process described above.

The thus obtained peptides of the present invention are utilizable as labelled antigens employed in radioimmunoassay (RIA) or enzyme immunoassay (EIA), by introducing thereto radioactive substances such as $^{125}I$, $^{131}I$, etc.; various enzyme reagents such as peroxidase (POX), chymotripsinogen, procarboxypeptidase, glyceraldehyde-3-phosphatedehydrogenase, amylase, phosphorylase, D-Nase, P-Nase, $\beta$-galactosidase, glucose-6-phosphate dehydrogenase, ornithine decarboxylase, etc. The introduction of the above radioactive substance can be effected in a conventional manner. For example, the introduction of radioactive iodine can be carried out by the oxidative iodination method using chloramine T, (W. M. Hunter and F. C. Greenwood, *Nature*, 194, 495 (1962), *Biochem. J.*, 89, 144 (1963)), etc. The introduction of enzyme reagents can be conducted by known methods such as conventional coupling reactions, e.g., the B. F. Erlanger, et al method (*Acta Endocrinol. Suppl.*, 168, 206 (1972)), the M. H. Karol et al method (*Proc. Natl. Acd. Sci. U.S.A.*, 57, 713 (1967)), etc.

Hereafter processes for production of antigens using the peptides of the present invention as haptens will be described in detail.

The aforesaid antigens are prepared by using the peptides of the present invention as haptens and reacting the peptides with a suitable carrier in the presence of a hapten-carrier binding agent. In this case, natural and synthetic proteins having a high molecular weight which are conventionally employed in the preparation of antigens can be widely employed as carriers to be bound to haptens. Examples of such carriers include albumins of animal sera such as horse serum albumin, bovine serum albumin, rabbit serum albumin, human serum albumin, sheep serum albumin, etc.; globulins of animal sera such as horse serum globulin, bovine serum globulin, rabbit serum globulin, human serum globulin, sheep serum globulin, etc.; thyroglobulins of animals such as horse thyroglobulin, bovine thyroglobulin, rabbit thyroglobulin, human thyroglobulin, sheep thyroglobulin, etc.; hemoglobulins of animals such as horse hemoglobulin, bovine hemoglobulin, rabbit hemoglobulin, human hemoglobulin, sheep hemoglobulin, etc.; hemocyanins of animals such as Keyhole limpet hemocyanin (KLH), etc; proteins extracted from ascaris (ascaris extracts, those described in Japanese Patent Application (OPI) No. 16414/81, *J. Immun.*, 111, 260–268 (1973), ibid., 122, 302–308 (1979), ibid., 98, 893–900 (1967) and *Am. J. Physiol.*, 199, 575–578 (1960), or purified products thereof); polylysine, polyglutamic acid, lysine-glutamic acid copolymers, copolymers containing lysine or ornithine, etc.

As hapten-carrier binding agents, those conventionally employed in the preparation of antigens can be widely employed. Specific examples of these agents include diazonium compounds for cross linking tyrosine, histidine, tryptophane, etc., e.g., bisdiazotized benzidine (BDB), bisdiazotized-3,3'-dianisidine (BDD), etc.; aliphatic dialdehydes for cross linking an amino group with an amino group, e.g., glyoxal, malonedialdehyde, glutaraldehyde, succinaldehyde, adipaldehyde, etc.; dimaleimide compounds for cross linking a thiol group with a thiol group, e.g., N,N'-o-phenylenedimaleimide, N,N'-m-phenylenedimaleimide, etc.; maleimidocarboxyl-N-hydroxysuccinimide esters for cross linking an amino group with a thiol group, e.g., metamaleimidobenzoyl-N-hydroxysuccinimide ester, 4-(maleimidomethyl)-cyclohexane-1-carboxyl-N'-hydroxysuccinimide ester, etc.; agents used in conventional peptide bond forming reactions in which amide bonds are formed from an amino group and a carboxyl group, e.g., dehydrating and condensing agents such as carbodiimides, e.g., N,N-dicyclohexylcarbodiimide, N-ethyl-N'-dimethylaminocarbodiimide, 1-ethyl-3-diisopropylaminocarbodiimide, 1-cyclohexyl-3-(2-morpholinyl-4-ethyl)carbodiimide, etc. As the foregoing hapten-carrier binding agent, it is also possible to use diazonium aryl carboxylic acids such as p-diazonium phenylacetic acid, etc. with conventional peptide bond forming agents such as the dehydrating and condensing agents described above in combination.

The reaction for preparing the antigens described above is carried out in an aqueous solution or a conventional buffer solution having pH of 7 to 10, preferably in a buffer solution having pH of 8 to 9, at temperatures of about 0° to 40° C., preferably around room temperature. The reaction is generally completed within about 1 to about 24 hours, preferably 3 to 5 hours. Representative examples of buffer solutions which can be used in the above process include:

0.2N sodium hydroxide-0.2M boric acid-0.2M potassium chloride buffer solution 0.2M sodium carbonate-0.2M boric acid-0.2M potassium chloride buffer solution 0.05M sodium tetraborate-0.2M boric acid-0.05M sodium chloride buffer solution 0.1M dihydrogen potassium phosphate-0.05M sodium tetraborate buffer solution In the above, proportions of the hapten, hapten-carrier binding agent and carrier can be appropriately determined but it is preferred that the carrier be employed in an amount of about 1 to about 6 times, preferably about 1 to about 5 times and the hapten-carrier binding agent be employed in an amount of about 5 to about 10 times, the weight of the hapten. By the above reaction, the carrier is bound to the hapten via the hapten-carrier binding agent to obtain a desired antigen composed of a peptide-carrier complex.

After completion of the reaction, the thus obtained antigen can easily be isolated and purified by means of a dialysis method, a gel filtration method, a fractionation precipitation method, etc.

The thus obtained antigen binds 5 to 60 mols in average of the peptide thereto per mole of a protein and enables one to subsequently prepare of an antibody having a high specificity to the antigen.

The preparation of an antibody using the antigen is carried out by administering the aforesaid antigen to mammals to thereby produce a desired antibody in vivo and collecting the antibody.

While there is no particular limitation to mammals provided for the preparation of antibodies, it is generally preferred to use rabbits or guinea pigs. In the production of antibodies, a definite amount of the antigen obtained as described above is diluted with a physiological saline solution to a suitable concentration and the resulting dilution is mixed with a complete Freund's adjuvant to prepare a suspension. The suspension is administered to mammals. For example, the aforesaid suspension is intracutaneously administered (1 to 5 mg/time as the amount of the antigen) to rabbit. Then the suspension is administered every two weeks over a period of 2 to 10 months, preferably 4 to 6 months to effect immunization. The collection of the antibody is carried out by collecting blood from the immunized animal after the passage of 1 to 2 weeks subsequent to the final administration, centrifuging the blood and isolating serum from the blood. According to this procedure, an antibody having an excellent specificity to the antigen used can be collected and used for assaying human leukemia virus-related proteins utilizing RIA, EIA, etc.

For purposes of explaining the present invention in more detail, preparations of the peptides shown by general formulae (1) to (6), antigens obtained from the peptides and antibodies will be shown by way of examples but the present invention is not deemed to be limited thereto.

Rf values in the respective preparation examples were measured using solvent mixtures described below by means of thin layer chromatography on silica gel.
$Rf^1$ ... n-butanol-acetic acid-water (4:1:5)
$Rf^2$ ... n-butanol-acetic acid-pyridine-water (15:3:10:12)

PREPARATION OF PEPTIDES

Synthesis Example 1

(1) In 14 ml of a DMSO solution of 5.88 milliequivalents of potassium tert-butoxide 1.54 g of Boc-Leu-OH was dissolved and 5 g of chloromethylated polystyrene resin (Protein Research Promotion Foundation) was added to the solution. The mixture was reacted at 80° C. for 30 minutes. After thoroughly washing the resin, in sequence, with DMSO, 50% acetic acid/chloroform and methylene chloride, the resin was dried under reduced pressure to obtain 5.06 g of Boc-Leu-resin.

A part of the Boc-Leu-resin was hydrolyzed and subjected to amino acid analysis. The results indicate that the product contained 0.30 mmol of the amino acid/g of the resin.

(2) After washing 2.17 g of the Boc-Leu-resin obtained in (1) above three times with 30 ml of chloroform, the resin was added to 30 ml of a chloroform solution of 50% trifluoroacetic acid (TFA) and the mixture was reacted at room temperature for 20 minutes. The reaction mixture was washed once with 30 ml of chloroform, 5 times with 30 ml of methylene chloride, 3 times with 30 ml of a methylene chloride solution of 10% triethylamine and then 6 times with 30 ml of methylene chloride to obtain H-Leu-resin.

To 25 ml of a solution of 0.35 g of Boc-Val-OH in methylene chloride the H-Leu-resin described above was added and 5 ml of a solution of 0.33 g of DCC in methylene chloride was then added to the resulting mixture. The mixture was reacted at room temperature for 2 hours. After washing the resin 6 times with 30 ml of methylene chloride, the resin was added to 25 ml of a methylene chloride solution of 0.35 g of Boc-Val-OH and 0.55 g of 1-hydroxybenzotriazole. Then, 5 ml of a methylene chloride solution of 0.33 g of DCC was added thereto and the resulting mixture was again reacted in a similar manner (double coupling). The resin was thoroughly washed with methylene chloride to obtain Boc-Val-Leu-resin.

(3) In a manner similar to (2) described above, des-Boc of the Boc-Val-Leu-resin was conducted and amino acids described below were then condensed in order, each followed by conducting des-Boc.

| | |
|---|---|
| Boc—Gln—ONP | 0.59 g |
| Boc—Pro—OH | 0.35 g |
| Boc—Ala—OH | 0.31 g |
| Boc—Thr(Bzl)—OH | 0.50 g |
| Boc—Pro—OH | 0.35 g |
| Boc—Glu(OBzl)—OH | 0.55 g |
| Boc—Val—OH | 0.35 g |
| Boc—Tyr(Cl₂—Bzl)—OH | 0.71 g |

Thus 2.65 g of H-Tyr(Cl₂-Bzl)-Val-Glu(OBzl)-Pro-Thr(Bzl)-Ala-Pro-Gln-Val-Leu-resin was obtained. 1.35 g of which was dissolved in 3 ml of anisole and 30 ml of hydrogen fluoride. After reacting the mixture at −20° C. for 30 minutes and then at 0° C. for 30 minutes, hydrogen fluoride was removed by distillation. The residue was extracted with 10% acetic acid and the extract was washed with ether. The aqueous layer was freeze dried and then purified by gel filtration using Sephadex G-10 (manufactured by Pharmacia Co., Ltd.; eluting liquid, 10% aqueous acetic acid solution), partition chromatography using Sephadex G-25 (manufactured by Pharmacia Co., Ltd.; eluting liquid, BuOH:AcOH:H₂O=4:1:5) and further with LH-20 (manufactured by Pharmacia Co., Ltd.; eluting liquid, 1/1000 N-HCl) to obtain H-Tyr-Val-Glu-Pro-Thr-Ala-Pro-Gln-Val-Leu-OH (hereafter referred to as "Peptide A").

Rf values: $Rf^1 = 0.12$; $Rf^2 = 0.58$

| | Elemental Analysis: (as $C_{52}H_{81}O_{16}N_{11}.7H_2O$) | | |
|---|---|---|---|
| | C (%) | H (%) | N (%) |
| Calcd. | 50.27 | 7.71 | 12.40 |
| Found | 50.41 | 7.83 | 12.41 |

Amino Acid Analysis (analyzed with Hitachi 835 Model)

| | Analytical Data |
|---|---|
| Ala (1) | 1.01 |
| Gln (1) | 2.09* |
| Glu (1) | |
| Leu (1) | 0.99 |
| Pro (2) | 2.04 |
| Thr (1) | 1.04 |
| Tyr (1) | 0.98 |

-continued

| | Analytical Data |
|---|---|
| Val (2) | 1.84 |

*Detected as Glu

SYNTHESIS EXAMPLE 2

In a manner similar to Synthesis Example 1-(1) and (2), each of the amino acids described below were condensed, in sequence, with 1.70 g of the Boc-Val-resin (0.296 mmol/g resin) obtained in a manner similar to Synthesis Example 1-(1) followed by des-Boc.

| | |
|---|---|
| Boc—Glu(OBzl)—OH | 0.43 g |
| Boc—Gly—OH | 0.22 g |
| Boc—Gly—OH | 0.22 g |
| Boc—Ile—OH(½H$_2$O) | 0.31 g |
| Boc—Ser(Bzl)—OH | 0.38 g |
| Boc—Asn—ONP | 0.46 g |
| Boc—Lys(Cl—Z)—OH | 0.53 g |
| Boc—Pro—OH | 0.28 g |
| Boc—His(Tos)—OH | 0.52 g |
| Boc—Pro—OH | 0.28 g |
| Boc—Ile—OH(½H$_2$O) | 0.31 g |

Thus 2.25 g of H-Ile-Pro-His(Tos)-Pro-Lys(Cl-Z)-Asn-Ser(Bzl)-Ile-Gly-Gly-Glu(OBzl)-Val-resin was obtained, 0.81 g of which was mixed with 15 ml of hydrogen fluoride and 1.5 ml of anisole. The mixture was reacted at −20° C. for 30 minutes and then at 0° C. for 30 minutes. After removing an excess of hydrogen fluoride by distillation, the residue was extracted with 10% acetic acid. After washing the extract with ether, the system was freeze dried. Then, purification was conducted by gel filtration with Sephadex G-25 (1M acetic acid) and then using CM-Cellulose 23 (manufactured by Watmann Co., Ltd., 0.04M AcONH$_4$, pH=7.2) to obtain H-Ile-Pro-His-Pro-Lys-Asn-Ser-Ile-Gly-Gly-Glu-Val-OH (hereafter referred to as "Peptide B").

Rf value: Rf$^1$=0.01; Rf$^2$=0.42

| Elemental Analysis: (as C$_{55}$H$_{90}$O$_{17}$N$_{16}$.8H$_2$O) | | | |
|---|---|---|---|
| | C (%) | H (%) | N (%) |
| Calcd. | 47.47 | 7.68 | 16.10 |
| Found | 47.39 | 7.71 | 15.98 |

Amino Acid Analysis (analyzed with Hitachi 835 Model)

| | Analytical Data |
|---|---|
| Asn (1) | 0.90* |
| Gly (2) | 1.99 |
| His (1) | 1.02 |
| Ile (2) | 2.02 |
| Lys (1) | 1.01 |
| Pro (2) | 1.99 |
| Ser (1) | 0.91 |
| Val (1) | 1.01 |
| Glu (1) | 1.02 |

*Detected as Asp

SYNTHESIS EXAMPLE 3

In a manner similar to Synthesis Example 1-(2), 0.19 g of Boc-Tyr(Cl$_2$-Bzl)-OH was reacted with 0.77 g of H-Ile-Pro-His(Tos)-Pro-Lys(Cl-Z)-Asn-Ser(Bzl)-Ile-Gly-Gly-Glu (OBzl)-Val-resin obtained in the same manner as in Synthesis Example 2 by double coupling. Then, the Boc group was split off with TFA to obtain 0.82 g of H-Tyr(Cl$_2$-Bzl)-Ile-Pro-His(Tos)-Pro-Lys(Cl-Z)-Asn-Ser(Bzl)-Ile-Gly-Gly-Glu(OBzl)-Val-resin. The thus obtained resin was mixed with 15 ml of hydrogen fluoride and 1.5 ml of anisole. The mixture was reacted at −20° C. for 30 minutes and then at 10° C. for 30 minutes. After removing an excess of hydrogen fluoride by distillation, the residue was extracted with 10% acetic acid. After washing the extract with ether, the system was freeze dried. Then, purification was conducted by gel filtration with Sephadex G-25 (1M acetic acid) and then using CM-Sephadex G-25 (0.04M AcONH$_4$, pH=7.2) to obtain H-Tyr-Ile-Pro-His-Pro-Lys-Asn-Ser-Ile-Gly-Gly-Glu-Val-OH (hereafter referred to as "Peptide C").

Rf Values: Rf$^1$=0.02; Rf$^2$=0.47

| Elemental Analysis: (as C$_{64}$H$_{99}$O$_{19}$N$_{17}$.8H$_2$O) | | | |
|---|---|---|---|
| | C (%) | H (%) | N (%) |
| Calcd. | 49.44 | 7.46 | 15.32 |
| Found | 49.43 | 7.56 | 15.06 |

Amino Acid Analysis (analyzed with Hitachi 835 Model)

| | Analytical Data |
|---|---|
| Asn (1) | 0.89* |
| Gly (2) | 1.99 |
| Glu (1) | 1.02 |
| His (1) | 1.02 |
| Ile (2) | 2.04 |
| Lys (1) | 1.02 |
| Pro (2) | 2.32 |
| Ser (1) | 0.91 |
| Val (1) | 1.01 |
| Tyr (1) | 1.05 |

*Detected as Asp

SYNTHESIS EXAMPLE 4

In a manner similar to Synthesis Example 1-(1), Boc-Leu-resin was prepared. Each of amino acids shown below was reacted, in sequence, with 2.17 g of the thus obtained resin by double coupling in a manner similar to Synthesis Example 1-(2) and (3) described above. The des-Boc reaction of the Trp-containing peptide was carried out in the presence of ethanedithiol.

| | |
|---|---|
| Boc—Val—OH | 0.35 g |
| Boc—Lys(Cl—Z)—OH | 0.66 g |
| Boc—Thr(Bzl)—OH | 0.50 g |
| Boc—Lys(Cl—Z)—OH | 0.66 g |
| Boc—Asp(OBzl)—OH | 0.52 g |
| Boc—Lys(Cl—Z)—OH | 0.66 g |
| Boc—Pro—OH | 0.35 g |
| Boc—Thr(Bzl)—OH | 0.50 g |
| Boc—Trp—OH | 0.49 g |
| Boc—Thr(Bzl)—OH | 0.50 g |

Thus 3.01 g of H-Thr(Bzl)-Trp-Thr(Bzl)-Pro-Lys(Cl-Z)-Asp(OBzl)-Lys(Cl-Z)-Thr(Bzl)-Lys(Cl-Z)-Val-Leu-resin was obtained. In a mixture of 15 ml of hydrogen fluoride, 1.5 ml of anisole and 0.8 ml of ethanedithiol 1.10 g of the thus obtained resin was dissolved. The solution was reacted at −20° C. for 30 minutes and then at 0° C. for 30 minutes. After removing an excess of hydrogen fluoride by distillation, the residue was extracted with 10% acetic acid. After washing the extract with ether, the system was freeze dried. Then, purification was conducted by gel filtration with Sephadex G-25 (1M acetic acid), CM-Cellulose 23 (0.05M AcONH$_4$, pH=7.2) an LH-20 ($10^{-3}$ NHCl) to obtain H-Thr-Trp-Thr-Pro-Lys-Asp-Lys-Thr-Lys-Val-Leu-OH (hereafter referred to as "Peptide D").

Rf values: $Rf^1$=0.01; $Rf^2$=0.44

| Elemental Analysis: (as $C_{81}H_{101}O_{17}N_{15}.17H_2O$) | | | |
|---|---|---|---|
| | C (%) | H (%) | N (%) |
| Calcd. | 45.15 | 8.39 | 12.95 |
| Found | 45.12 | 8.65 | 12.89 |

Amino Acid Analysis (analyzed with Hitachi 835 Model)

| | Analytical Data |
|---|---|
| Asp (1) | 0.91 |
| Lys (3) | 3.20 |
| Leu (1) | 1.00 |
| Pro (1) | 1.00 |
| Thr (3) | 2.89 |
| Trp (1) | 0.93 |
| Val (1) | 0.98 |

SYNTHESIS EXAMPLE 5

Boc-Tyr(Cl$_2$-Bzl)-OH, 0.13 g, was reacted with 0.55 g of H-Thr(Bzl)-Trp-Thr(Bzl)-Pro-Lys(Cl-Z)-Asp(OBzl)-Lys(Cl-Z)-Thr(Bzl)-Lys(Cl-Z)-Val-Leu-resin obtained in the same manner as in Synthesis Example 4 by double coupling. Then the Boc group was split off with TFA in the presence of ethanedithiol to obtain 0.59 g of H-Thr(Cl$_2$-Bzl)-Trp-Thr (Bzl)-Pro-Lys(Cl-Z)-Asp(OBzl)-Lys(Cl-Z)-Thr(Bzl)-Lys(Cl-Z)-Val-Leu-resin.

The thus obtained resin was dissolved in a mixture of 15 ml of hydrogen fluoride, 1.5 ml of anisole and 0.8 ml of ethanedithiol. The solution was reacted at −20° C. for 30 minutes and then at 0° C. for 30 minutes. After removing an excess of hydrogen fluoride by distillation, the residue was extracted with 10% acetic acid. After washing the extract with ether, the system was freeze dried. Then, purification was conducted with CM-Cellulose 23 (0.05M AcONH$_4$, pH=7.2) and LH-20 ($10^{-3}$ NHCl) to obtain H-Tyr-Thr-Trp-Thr-Pro-Lys-Asp-Lys-Thr-Lys-Val-Leu-OH (hereafter referred to as "Peptide E").

Rf values: $Rf^1$=0.01; $Rf^2$=0.47

| Elemental Analysis: (as $C_{70}H_{110}O_{19}N_{16}.17H_2O$) | | | |
|---|---|---|---|
| | C (%) | H (%) | N (%) |
| Calcd. | 47.08 | 8.13 | 12.55 |
| Found | 46.89 | 8.34 | 12.54 |

Amino Acid Analysis (analyzed with Hitachi 835 Model)

| | Analytical Data |
|---|---|
| Asp (1) | 0.91 |
| Lys (3) | 3.10 |
| Leu (1) | 1.02 |
| Pro (1) | 1.20 |
| Thr (3) | 2.85 |
| Trp (1) | 0.92 |
| Val (1) | 0.93 |

Synthesis Example 6

(1) In 42 ml of a DMSO solution of 15.33 milliequivalents of potassium tert-butoxide 7.53 g of Boc-Tyr(Cl$_2$-Bzl)-OH was dissolved and 10 g of chloromethylated polystyrene resin (Protein Research Promotion Foundation) was added to the solution. The mixture was reacted at 80° C. for 30 minutes. After thoroughly washing the resin, in sequence, with DMSO, 50% acetic acid/chloroform and methylene chloride, the resin was dried under reduced pressure to obtain 12 g of Boc-Tyr(Cl$_2$-Bzl)-resin.

A part of the thus obtained resin was hydrolyzed and subjected to amino acid analysis. The results indicate that the product contained 0.31 mmol of the amino acid/g of the resin.

(2) After washing 1.70 g of the Boc-Tyr(Cl$_2$-Bzl)-resin obtained in (1) above three times with 30 ml of chloroform, the resin was added to 30 ml of a chloroform solution of 50% trifluoroacetic acid (TFA) and the mixture was reacted at room temperature for 20 minutes. The reaction mixture was washed once with 30 ml of chloroform, 5 times with 30 ml of methylene chloride, 3 times with 30 ml of a methylene chloride solution of 10% triethylamine and then 6 times with 30 ml of methylene chloride to obtain H-Tyr(Cl$_2$-Bzl)-resin.

To 25 ml of a solution of 0.28 g of Boc-Pro-OH in methylene chloride the H-Tyr(Cl$_2$-Bzl)-resin described above was added and 5 ml of a solution of 0.27 g of DCC in methylene chloride was then added to the resulting mixture. The mixture was reacted at room temperature for 2 hours. After washing the resin 6 times with 30 ml of methylene chloride, the resin was added to 25 ml of a methylene chloride solution of 0.28 g of Boc-Pro-OH and 0.55 g of 1-hydroxybenzotriazole. Then, 5 ml of a methylene chloride solution of 0.27 g of DCC was added thereto and the resulting mixture was again reacted in a similar manner (double coupling). The resin was thoroughly washed with methylene chloride to obtain Boc-Pro-Tyr(Cl$_2$-Bzl)-resin.

(3) In a manner similar to (2) described above, des-Boc of the Boc-Pro-Tyr(Cl$_2$-Bzl)-resin was conducted. Then, amino acids, amino acids wherein functional groups at the side chain thereof were protected or carboxyl groups were activated, described below were condensed in order, followed by conducting des-Boc.

| Boc—Pro—OH | 0.28 g |
|---|---|
| Boc—Pro—OH | 0.28 g |
| Boc—Lys(Cl—Z)—OH | 0.55 g |
| Boc—Lys(Cl—Z)—OH | 0.55 g |
| Boc—Pro—OH | 0.28 g |
| Boc—Gln—ONP | 0.48 g |
| Boc—Val—OH | 0.29 g |
| Boc—Val—OH | 0.29 g |

Thus 2.57 g of H-Val-Val-Gln-Pro-Lys(Cl-Z)-Lys(Cl-Z)-Pro-Pro-Pro-Tyr(Cl$_2$-Bzl)-resin. The thus obtained resin, 1.20 g, was dissolved in a mixture of 2 ml of anisole and 20 ml of hydrogen fluoride. The solution was incubated at −20° C. for 30 minutes and then at 0° C. for 30 minutes. Thereafter an excess of hydrogen fluoride was removed by distillation. The residue was extracted with 10% acetic acid and the extract was washed with ether. The aqueous layer was freeze dried and then purified by gel filtration using Sephadex G-25 (manufactured by Pharmacia Co., Ltd.; eluting liquid, 1M acetic acid) and further using CM-23 Cellulose (manufactured by Whatman Co., Ltd.; eluting liquid, 0.04M ammonium acetate; pH=7.2) to obtain 162 mg of H-Val-Val-Gln-Pro-Lys-Lys-Pro-Pro-Pro-Tyr-OH (hereafter referred to as "Peptide F").

Rf values: $Rf^1$=0.01; $Rf^2$=0.27

| Elemental Analysis: (as $C_{56}H_{89}O_{13}N_{13}.3CH_3CO_2H.4H_2O$) | | | |
|---|---|---|---|
|  | C (%) | H (%) | N (%) |
| Calcd. | 53.02 | 7.82 | 12.96 |
| Found | 52.94 | 8.06 | 12.74 |

Amino acid analysis (analyzed with Hitachi 835 Model)

|  | Analytical Data |
|---|---|
| Gln (1) | 1.05* |
| Lys (2) | 2.17 |
| Pro (4) | 4.02 |
| Tyr (1) | 1.05 |
| Val (2) | 1.69 |

*Detected as Glu

Synthesis Example 7

In a manner similar to Synthesis Example 6-(1), Boc-Pro-resin (0.44 mmol/g resin) was prepared. Each of amino acids or derivatives thereof shown below was reacted, in sequence, with 1.20 g of the thus obtained resin by double coupling in a manner similar to Synthesis Example 6-(2) and (3) described above. The des-Boc reaction was then carried out.

| | |
|---|---|
| Boc—Ser(Bzl)—OH | 0.39 g |
| Boc—Ala—OH | 0.25 g |
| Boc—Ser(Bzl)—OH | 0.39 g |
| Boc—Arg(Tos)—OH | 0.56 g |
| Boc—Ser(Bzl)—OH | 0.39 g |
| Boc—Phe—OH | 0.35 g |
| Boc—Ile—OH ½$H_2O$ | 0.32 g |
| Boc—Gln—ONP | 0.49 g |
| Boc—Gly—OH | 0.23 g |
| Boc—Met—OH | 0.33 g |

Thus 1.58 g of H-Met-Gly-Gln-Ile-Phe-Ser(Bzl)-Arg(Tos)-Ser(Bzl)-Ala-Ser(Bzl)-Pro-resin was obtained. In a mixture of 10 ml of hydrogen fluoride, 0.5 ml of 1,2-ethanedithiol and 1 ml of anisole 0.40 g of the thus obtained resin was dissolved. The solution was incubated at −20° C. for 30 minutes and then at 0° C. for 30 minutes. After removing an excess of hydrogen fluoride by distillation under reduced pressure, the residue was extracted with 10% acetic acid. After washing the extract with ether, the system was freeze dried.

Then, purification was conducted by gel filtration with Sephadex G-25 (manufactured by Pharmacia Co., Ltd.; eluting liquid, 1M acetic acid) and CM-Cellulose 23 (manufactured by Whatmann Co., Ltd.; 0.1 to 0.5M ammonium acetate, pH=5.0, linear concentration gradient) to obtain 32 mg of H-Met-Gly-Gln-Ile-Phe-Ser-Arg-Ser-Ala-Ser-Pro-OH (hereafter referred to as "Peptide G").

Rf values: $Rf^1$=0.01; $Rf^2$=0.50

| Elemental Analysis: (as $C_{50}H_{81}O_{16}N_{15}S.CH_3CO_2H.5H_2O$) | | | |
|---|---|---|---|
|  | C (%) | H (%) | N (%) |
| Calcd. | 46.94 | 7.20 | 15.79 |
| Found | 47.01 | 7.32 | 15.66 |

Amino acid analysis (analyzed with Hitachi 835 Model)

|  | Analytical Data |
|---|---|
| Ala (1) | 1.07 |
| Arg (1) | 1.07 |
| Gln (1) | 1.00* |
| Gly (1) | 1.00 |
| Ile (1) | 0.91 |
| Met (1) | 0.94 |
| Phe (1) | 0.93 |
| Pro (1) | 1.07 |
| Ser (3) | 2.98 |

*Detected as Glu

Synthesis Example 8

In a manner similar to Synthesis Example 6-(2) described above, 0.47 g of Boc-Tyr($Cl_2$-Bzl)-OH was reacted with 0.41 g of H-Met-Gly-Gln Ile-Phe-Ser(Bzl)-Arg(Tos)-Ser(Bzl)-Ala-Ser(Bzl)-Pro-resin by double coupling. Then, the Boc group was split off with trifluoroacetic acid to obtain H-Tyr($Cl_2$-Bzl)-Met-Gly-Gln-Ile-Phe-Ser(Bzl)-Arg(Tos)-Ser(Bzl)-Ala-Ser(Bzl)-Pro-resin. The thus obtained resin was mixed with a mixture of 10 ml of hydrogen fluoride, 1 ml of anisole and 0.5 ml of 1,2-ethanedithiol. The mixture was incubated at −30° C. for 30 minutes and then at 0° C. for 30 minutes. After removing an excess of hydrogen fluoride by distillation under reduced pressure, the residue was extracted with 10% acetic acid. After washing the extract with ether, the system was freeze dried. Then, purification was conducted by gel filtration with Sephadex G-25 (manufactured by Pharmacia Co., Ltd., 1M acetic acid) and then by HPLC using a debelogil column (manufactured by Chemco Co., Ltd.; eluting liquid, 0.1M $NaH_2PO_4$: acetonitrile=80:20). Thereafter, the purified matter was desalted with Sephadex G-25 (manufactured by Pharmacia Co., Ltd.; eluting liquid, 1M acetic acid) to obtain 9.23 mg of H-Tyr-Met-Gly-Gln-Ile-Phe-Ser-Arg-Ser-Ala-Ser-Pro-OH (hereafter referred to as "Peptide H").

Rf values: $Rf^1$=0.01; $Rf^2$=0.52

| Elemental Analysis: (as $C_{59}H_{90}O_{18}N_{16}S.CH_3CO_2H.6H_2O$) | | | |
|---|---|---|---|
|  | C (%) | H (%) | N (%) |
| Calcd. | 48.47 | 7.07 | 14.82 |
| Found | 48.63 | 7.01 | 14.77 |

Amino acid analysis (analyzed with Hitachi 835 Model)

| Analytical Data | |
|---|---|
| Ala (1) | 1.03 |
| Met (1) | 1.00 |
| Arg (1) | 1.07 |
| Phe (1) | 1.09 |
| Gln (1) | 1.03* |
| Pro (1) | 0.99 |
| Gly (1) | 1.14 |
| Ser (3) | 2.68 |
| Ile (1) | 1.03 |
| Tyr (1) | 1.03 |

*Detected as Glu

Synthesis Example 9

In a manner similar to Example 6-(1), 0.27 mmol/g resin of Boc-Leu-resin was prepared. Each of amino acids or derivatives thereof described below were reacted, in sequence, with 2 g of the Boc-Leu-resin by double coupling in a manner similar to Synthesis Example 6-(2) and (3). Then des-Boc reaction followed.

| | |
|---|---|
| Boc—Ser—OH | 0.40 g |
| Boc—Arg(Tos)—OH | 0.58 g |
| Boc—Leu—OH.H$_2$O | 0.34 g |
| Boc—Ile—OH.½H$_2$O | 0.32 g |
| Boc—Pro—OH | 0.29 g |
| Boc—Asp(OBzl)—OH | 0.44 g |
| Boc—Lys(Cl—Z)—OH | 0.56 g |
| Boc—Pro—OH | 0.29 g |
| Boc—Thr(Bzl)—OH | 0.39 g |
| Boc—Gly—OH | 0.24 g |
| Boc—Glu(OBzl)—OH | 0.46 g |
| Boc—Pro—OH | 0.29 g |
| Boc—Tyr(Cl$_2$—Bzl)—OH | 0.57 g |

Thus 2.62 g of Boc-Tyr(Cl$_2$-Bzl)-Pro-Glu(OBzl)-Gly-Thr(Bzl)-Pro-Lys(Cl-Z)-Asp(OBzl)-Pro-Ile-Leu-Arg(Tos)-Ser-Leu-resin was obtained. In a mixture of 20 ml of hydrogen fluoride and 2 ml of anisole 1.62 g of the thus obtained resin was dissolved. The solution was reacted at −20° C. for 30 minutes and then at 0° C. for 30 minutes. After removing an excess of hydrogen fluoride by distillation under reduced pressure, the residue was extracted with 10% acetic acid. After washing the extract with ether, the system was freeze dried. Then, purification was conducted by gel filtration with Sephadex G-25 (1M acetic acid) and then HPLC using debelogil column (eluting liquid, 0.1M phosphite buffer: acetonitrile=80:20) to obtain 104 mg of a peptide, H-Tyr-Pro-Glu-Gly-Thr-Pro-Lys-Asp-Pro-Ile-Leu-Arg-Ser-Leu-OH (hereafter referred to as "Peptide I").

Rf values: Rf$^1$=0.01; Rf$^2$=0.42

| Elemental Analysis: (as C$_{72}$H$_{116}$O$_{22}$N$_{18}$.CH$_3$CO$_2$H.7H$_2$O) | | | |
|---|---|---|---|
| | C (%) | H (%) | N (%) |
| Calcd. | 50.16 | 7.62 | 14.23 |
| Found | 49.87 | 7.60 | 14.29 |

Amino acid analysis (analyzed with Hitachi 835 Model)

| | Analytical Data |
|---|---|
| Asp (1) | 0.96 |
| Lys (1) | 1.13 |
| Arg (1) | 1.02 |
| Pro (3) | 2.79 |

| Analytical Data | |
|---|---|
| Glu (1) | 1.05 |
| Ser (1) | 0.92 |
| Gly (1) | 1.03 |
| Thr (1) | 0.99 |
| Ile (1) | 0.99 |
| Tyr (1) | 0.97 |
| Leu (2) | 2.11 |

Synthesis Examle 10

The same procedures as in Synthesis Example 9 were repeated except that 0.58 g of Boc-Ser(Bzl)-OH was used in place of 0.40 g of Boc-Ser-OH to obtain 120 mg of Peptide I having the same physical properties as above.

Preparation of Antigen

Preparation Example 1

To 3.0 ml of a 0.05M phosphate buffer (pH=7.0) 5 mg of Peptide A obtained in Synthesis Example 1 and 12 mg of KLH (Sigma Co., Ltd.) were added and 0.2 ml of a 2% glutaraldehyde (GA) solution was dropwise added to the resulting solution. The mixture was stirred at room temperature for 3 hours. Thereafter the reaction mixture was dialyzed at 4° C. against distilled water overnight. After freeze drying, 16.5 mg of an antigen was obtained. The antigen is hereafter referred to as "Antigen A".

Antigen A bound thereto 10 mols of Peptide A per mol of KLH (when an average molecular weight was made 100,000) in average. This binding rate of Peptide A to the KLH was determined as follows: A fraction of Peptide A bound to the KLH was separated from another fraction of other product (dimer of Peptide A) by gel filtration of Antigen A obtained with Sephadex G-50 (eluting liquid, physiological saline solution; detection, OD 280 nm; eluting rate, 3 ml/hour; fractionated amount, 1 ml each); a calibration curve of a peptide dimer having standard concentrations was prepared to determine the amount of the aforesaid dimer; and the thus determined amount of the dimer was subtracted from the amount of Peptide A used as a raw material, assuming that the thus subtracted amount would be all bound to the KLH since neither the unreacted KLH nor Peptide A was recognized. Such is hereafter the same also in the following examples for preparing antigens.

Preparation Example 2

(1) A BDB solution was prepared by adding 83.25 mg of benzidine to a solvent mixture of 20 ml of 0.2N-HCl and 3 ml of DMF, stirring the mixture under ice cooling, gradually adding 2 ml of distilled water containing 87.03 mg of sodium nitrite to the solution and then stirring the mixture for 30 minutes.

(2) In 1 ml of a 0.16M borate buffer (pH=9.0) containing 0.13M NaCl were dissolved 5.08 mg of Peptide E and 8.07 mg of KLH. The solution was slowly stirred at 4° C. To the solution 1 ml of the BDB solution obtained in (1) above was gradually added dropwise. The reaction solution was adjusted with 0.5N NaOH to pH=9.0 followed by reacting for further 2 hours at 4° C. Thereafter the reaction mixture was dialyzed at 4° C. against distilled water overnight. After freeze drying, 12.27 mg of an antigen was obtained. Hereafter the antigen is referred to as "Antigen B". Antigen B bound thereto 35 mols of Peptide E per mol of KLH in average.

Preparation Example 3

In a manner similar to Preparation Example 2 described above, 12.74 mg of an antigen was obtained except for using 5.17 mg of Peptide C and 8.03 mg of KLH. Hereafter the antigen is referred to as "Antigen C". Antigen C bound thereto 42 mols of Peptide C per mol of KLH in average.

Preparation Example 4

Following the preparation examples described above, antigens shown in Table 2 below were obtained.

TABLE 2

| Antigen | Hapten (mg) | Carrier (mg) | Binding Agent (mg) | Molar Ratio of Carrier-Hapten Bond |
|---|---|---|---|---|
| D | Peptide A (3) | ASC (6) | GA (0.59) | 1:24 |
| E | Peptide E (2) | ASC (4) | BDB (0.75) | 1:14 |
| F | Peptide A (3) | ASC (6) | BDB (1.50) | 1:18 |
| G | Peptide B (3) | ASC (6) | DCC (0.67) | 1:25 |
| H | Peptide C (3) | ASC (6) | BDB (1.19) | 1:22 |
| I | Peptide D (3) | ASC (6) | DCC (0.50) | 1:16 |

ASC: Ascaris extracts having an average molecular weight of 100,000.

Preparation Example 5

To 3.0 ml of a 0.05M phosphate buffer (pH=7.0) 5.09 mg of Peptide G obtained in Synthesis Example 7 and 25.10 mg of KLH were added and 0.2 ml of a 2% glutaraldehyde solution was dropwise added to the resulting solution. The mixture was stirred at room temperature for 3 hours. Thereafter the reaction mixture was dialyzed at 4° C. with distilled water overnight. After freeze drying, 26.49 mg of the desired antigen was obtained. The antigen is hereafter referred to as "Antigen J".

Antigen J bound thereto 10 mols of Peptide G per mol of KLH (when an average molecular weight was made 100,000) in average.

Preparation Example 6

(1) A BDB solution was prepared by adding 83.25 mg of benzidine to a solvent mixture of 20 ml of 0.2N-HCl and 3 ml of DMF, stirring the mixture under ice cooling, gradually adding 2 ml of distilled water containing 87.03 mg of sodium nitrite to the solution and then stirring the mixture for 30 minutes.

(2) In 1 ml of a 0.16M borate buffer (pH=9.0) containing 0.13M NaCl were dissolved 5.13 mg of Peptide I and 8.10 mg of KLH. The solution was slowly stirred at 4° C. To the solution 0.5 ml of the BDB solution obtained in (1) above was gradually added dropwise. The reaction solution was adjusted with 0.5N NaOH to pH=9.0 followed by reacting for further 2 hours at 4° C. Thereafter the reaction mixture was dialyzed at 4° C. against distilled water overnight. After freeze drying, 12.76 mg of the desired antigen was obtained. Hereafter the antigen is referred to as "Antigen K". Antigen K bound thereto 18 mols of Peptide I per mol of KLH in average.

Preparation Example 7

In a manner similar to Preparation Example 6 described above, 12.74 mg of an antigen was obtained except for using 5.17 mg of Peptide F and 8.03 mg of KLH. Hereafter the antigen is referred to as "Antigen L". Antigen L bound thereto 25 mols of Peptide F per mol of KLH in average.

Preparation Example 8

Following the preparation examples described above, antigens shown in Table 3 below were obtained.

TABLE 3

| Antigen | Hapten (mg) | Carrier (mg) | Binding Agent (mg) | Molar Ratio of Carrier-Hapten Bond |
|---|---|---|---|---|
| M | Peptide G (2) | ASC (4) | GA (0.37) | 1:19 |
| N | Peptide G (2) | ASC (4) | DCC (0.70) | 1:21 |
| O | Peptide I (2) | ASC (4) | DCC (0.57) | 1:17 |
| P | Peptide I (2) | ASC (4) | GA (0.30) | 1:14 |
| Q | Peptide I (2) | ASC (4) | BDB (0.69) | 1:13 |
| R | Peptide F (5) | ASC (10) | BDB (2.42) | 1:19 |
| S | Peptide H (3) | BSA (6) | DCC (0.40) | 1:22 |

PREPARATION OF ANTIBODY

Preparation Example 1

After dissolving 100 μg of each of Antigens A, B and C obtained in Preparation Examples (of Antigen) 1 to 3 in 1.5 ml of a physiological saline solution, respectively, 1.5 ml of a Freund's adjuvant was added to each of the solutions to obtain suspensions. Each of the suspensions was subcutaneously administered to several rabbits (New Zealand white rabbits), respectively. Each of the suspensions was given at the same dose 6 times every 2 weeks and then at the same dose as the initial dose 3 times monthly. Seven days after the final administration, blood was collected from the test animals. Antisera were obtained by centrifugation and the desired antibodies were obtained, respectively. Antibodies are referred to as follows: "Antibody A" which was obtained from Antigen A, "Antibody B", "Antibody C", "Antibody D", "Antibody E" and "Antibody F" from Antigen B; "Antibody G", "Antibody H", "Antibody I", "Antibody J" and "Antibody K" from Antigen C.

Preparation Example 2

Using each 500 μg of the antigens obtained in Preparation Example 4 of Antigen described above, antibodies shown in Table 4 below were obtained, respectively, in a manner similar to Preparation Example 1 of Antibody described above.

TABLE 4

| Antigen No. | Antibody No. |
|---|---|
| Antigen D | Antibody L |
|  | Antibody M |
|  | Antibody N |
| Antigen E | Antibody O |
|  | Antibody P |
|  | Antibody Q |
| Antigen F | Antibody R |
|  | Antibody S |
|  | Antibody T |

TABLE 4-continued

| Antigen No. | Antibody No. |
| --- | --- |
| Antigen G | Antibody U |
| Antigen H | Antibody V |
|  | Antibody W |
|  | Antibody X |
| Antigen I | Antibody Y |

Preparation Example 3

After dissolving 100 μg of each of Antigens J, K and L obtained in Preparation Examples (of Antigen) 5 to 7 in 1.5 ml of a physiological saline solution, respectively, 1.5 ml of a Freund's adjuvant was added to each of the solutions to obtain suspensions. Each of the suspensions was subcutaneously adminstered to several rabbits (New Zealand white rabbits) (2.5 to 3.0 kg), respectively. Each of the suspensions was given to the rabbits at the same dose level 6 times every 2 weeks and then at the same dose as the initial dose 3 times monthly. Seven days after the final administration, blood was collected from the test animals. Antisera were obtained by centrifugation and the desired antibodies were obtained, respectively. Antibodies are referred to as follows: "Antibody Z" which was obtained from Antigen J; "Antibody AA", "Antibody AB", "Antibody AC", "Antibody AD", and "Antibody AE" from Antigen K; and "Antibody AF" from Antigen L.

Preparation Example 4

Using each 500 μg of the antigens obtained in Preparation Example 8 of Antigen described above, antibodies shown in Table 5 below were obtained, respectively, in a manner similar to Preparation Example 3 of Antibody described above.

TABLE 5

| Antigen No. | Antibody No. |
| --- | --- |
| Antigen M | Antibody AG |
|  | Antibody AH |
| Antigen N | Antibody AI |
|  | Antibody AJ |
| Antigen O | Antibody AK |
|  | Antibody AL |
| Antigen P | Antibody AM |
|  | Antibody AN |
| Antigen Q | Antibody AO |
|  | Antibody AP |
| Antigen R | Antibody AQ |
|  | Antibody AR |
|  | Antibody AS |
|  | Antibody AT |
|  | Antibody AU |
| Antigen S | Antibody AV |

PREPARATION OF LABELLED PEPTIDE

Preparation Example 1

Peptides A, C, E, F, H and I obtained in Synthesis Examples 1, 3, 5, 6, 8 and 9, respectively were labelled in accordance with the method using chloramin T as follows:

That is, 20 μl of a 0.5M phosphate buffer containing 1 mCi of Na ($^{125}$I) (carrier free N.E.N.) was added to 10 μl of a 0.5M phosphate buffer (pH 7.5) containing 5 μg of the aforesaid peptide and then 20 μl of a 0.5M phospate buffer containing 20 μl of chloramin T was added thereto. After stirring the mixture for 25 seconds at room temperature, 20 μl of a 0.5M phosphate buffer containing 100 μg of sodium metabisulfite ($Na_2S_2O_5$) was added to the mixture to complete the reaction. Then, 10 μl of a cold 10% aqueous sodium iodide solution was added to the reaction mixture. The reaction mixture was passed through a Sephadex G-25 column (1.0 to 50 cm) (eluting liquid, a 0.2M ammonium acetate buffer containing 0.1% BSA and 0.01% $NaN_3$; pH 5.5) to obtain a Peptide labelled with $^{125}$I.

The radioactivity of each of the thus labelled peptides was not lower than 1,000 μCi/μg.

Measurement of Titer

The titer of each of the antibodies obtained as described above was measured as follows:

That is, each of the antibodies was diluted with a physiological saline solution to 10, $10^2$, $10^3$, $10^4$, $10^5$, . . . times, respectively. To 100 μl each of the thus obtained dilutions, were added 0.1 ml of a labelled peptide diluted to about 9500 cpm (Labelled Peptide A in the case of Antibodies A, L to N, R to T; Labelled Peptide C in the case of Antibodies G to K and U to X; Labelled Peptide E in the case of Antibodies B to F, O to Q and Y; Labelled Peptide F in the case of Antibodies AF and AQ to AU; Labelled Peptide H in the case of Antibodies Z, AG to AJ and AV; and Labelled Peptide I in the case of Antibodies AA to AE and AK to AP, respectively) and 0.2 ml of a 0.05M phosphate buffer (pH=7.4; containing 0.25% BSA, 10 mM EDTA and 0.02% $NaN_3$). The mixture was incubated at 4° C. for 24 hours. The resulting antibody-$^{125}$I-labelled peptide complex was separated from the unreacted (unbound) $^{125}$I-labelled peptide by the dextran-activated charcoal method and the centrifugal method (4° C., 30 minutes, 3000 rpm) and the radioactive ray was counted to measure a binding rate (%) of the antibody to the $^{125}$I-labelled peptide at each of the dilution concentrations. The binding rate (%) of the antibody to the $^{125}$I-labelled peptide is taken on the vertical axis and the dilution magnification of the antibody is taken on the abscissa. At each of the concentrations, the binding rate is plotted. Then, the dilution magnification of the antibody where the binding rate shows 50%, i.e., a titer of the antibody, is determined.

The results obtained are shown in Table 6 below.

TABLE 6

| Antibody No. | Titer |
| --- | --- |
| A | 5000 |
| B | 250 |
| C | 1500 |
| D | 32000 |
| E | 3400 |
| F | 5000 |
| G | 4200 |
| H | 720 |
| I | 1800 |
| J | 420 |
| K | 750 |
| L | 62500 |
| M | 16500 |
| N | 2300 |
| O | 7500 |
| P | 18500 |
| Q | 1800 |
| R | 11750 |
| S | 2500 |
| T | 3250 |
| U | 3000 |
| V | 19000 |
| W | 2500 |
| X | 9000 |
| Y | 3500 |
| Z | 1000 |
| AA | 1500 |

TABLE 6-continued

| Antibody No. | Titer |
| --- | --- |
| AB | 50 |
| AC | 5000 |
| AD | 2500 |
| AE | 1000 |
| AF | 7500 |
| AG | 780 |
| AH | 2550 |
| AI | 15000 |
| AJ | 2700 |
| AK | 175 |
| AL | 125 |
| AM | 1000 |
| AN | 2650 |
| AO | 5250 |
| AP | 6000 |
| AQ | 2100 |
| AR | 675 |
| AS | 9500 |
| AT | 70000 |
| AU | 550 |
| AV | 10000 |

Test for ATLA Specificity of Antibody (1) Peptide A, D or F having various concentrations and ATLA samples described below were employed as samples.

ATLA Positive Sample

To $5 \times 10^9$ of cultured cells of ATLA positive cell line YAM [Science, 217, pp. 737–739 (1982)] 30 ml of a physiological saline solution was added followed by homogenization. Then the mixture was centrifuged (105000×g) for 1 hour to collect the supernatant. The amount of the proteins in the supernatant was adjusted with PBS to 10 mg/ml (the amount of the proteins was measured by a coloration method using a reagent for total protein assay made by the Otsuka Assay Research Laboratories, "Tonein-TP") (hereafter the supernatant is referred to as "YAM Supernatant").

Further, a 0.05M phosphate buffer (pH 7.4) containing 0.25% BSA, 5 mM EDTA and 0.02% NaN₃ was employed as a standard diluting solution.

In each of test tubes, 0.2 ml of the standard diluting solution, 0.1 ml of a sample, 0.1 ml of Antibody L, O or AT obtained in Preparation Example (of Antibody) diluted so as to give a titer of 50,000 in finally obtained assay system and 0.1 ml of ¹²⁵I-labelled peptide corresponding to the above-described antibody (a dilution obtained by diluting Labelled Peptide A, E or F obtained as described above to about 10000 cpm) were charged. After incubating the mixture at 4° C. for 72 hours, 0.1 ml of normal porcine serum was added thereto. Then, 0.5 ml of a suspension of activated charcoal coated with dextran was added to the mixture. The mixture was allowed to stand for 30 minutes at 4° C. Thereafter, the mixture was centrifuged at 4° C. for 30 minutes at 3000 rpm to separate the antibody-¹²⁵I-labelled peptide complex (B) from the unreacted (unbound) ¹²⁵I-labelled peptide (F). The radioactive ray of the complex was counted to determine a percentage of (B) at each concentration and dilution of the respective samples. The results obtained are shown in FIGS. 1 to 3.

In each of the figures, the vertical axis represents a binding % (B/Bo×100 wherein Bo is a percentage of (B) when the concentration of a sample is made 0) and the abscissa represents concentrations of samples (concentration of Peptide A, D or F and, protein contents of YAM Supernatant).

Figure 1:
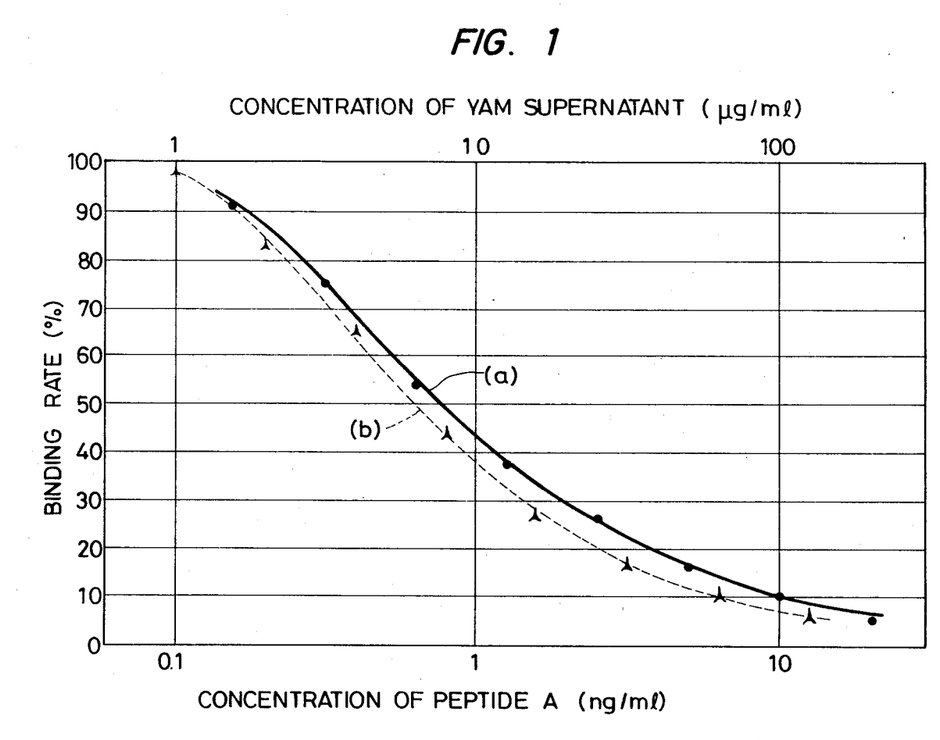
FIGS. 1 to 3 are curves showing the reactivity (specificity) of the antibody of the present invention to ATL-associaed antigen (ATLA) and Peptide A, D or F.

FIG. 1 shows results of ATLA specificity test using Antibody L; curves (a) and (b) represent Peptide A and YAM Supernatant, respectively.

Figure 2:
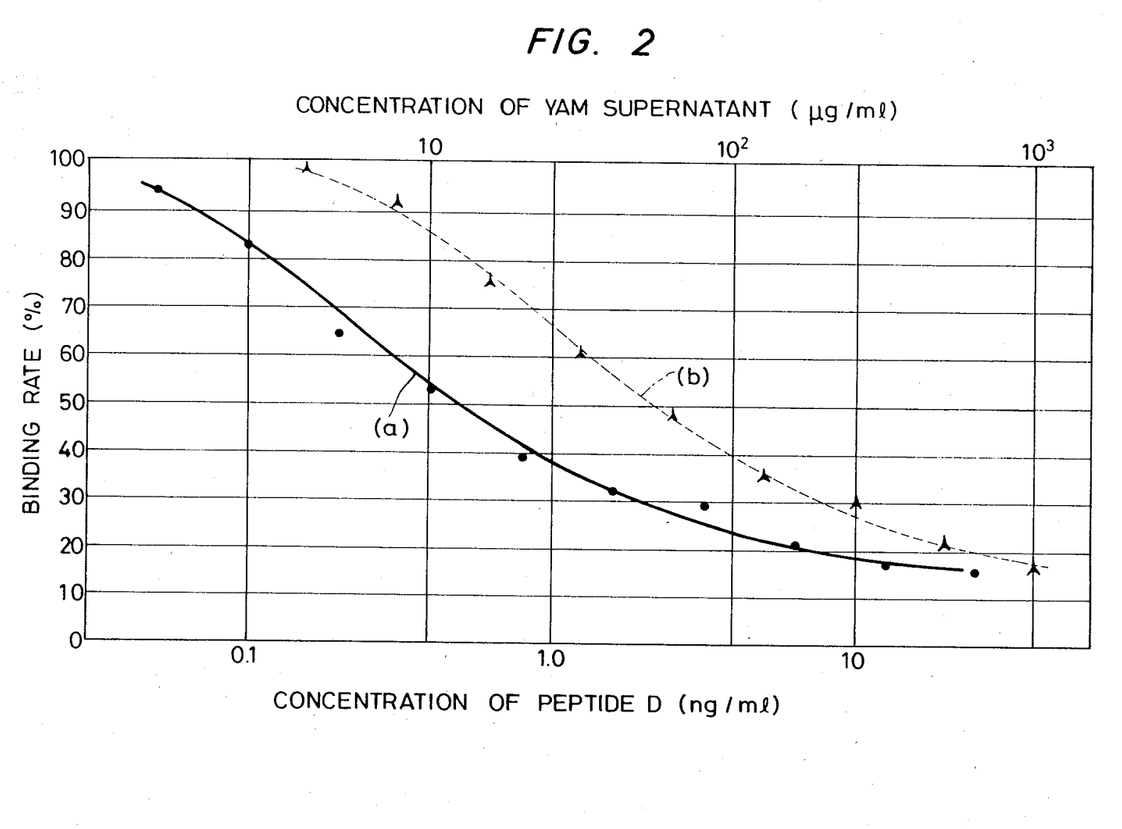
Figure 3:
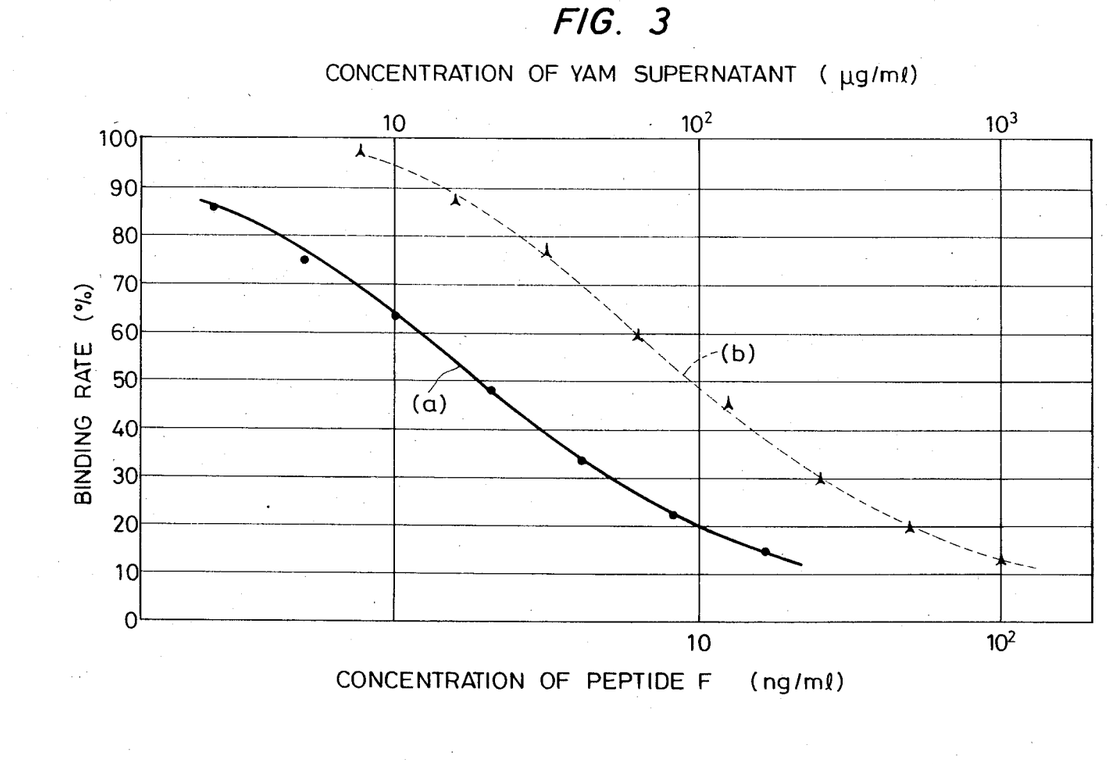

FIG. 2 shows results of ATLA specificity test using Antibody O; curves (a) and (b) represent Peptide D and YAM Supernatant, respectively.

FIG. 3 shows results of ATLA specificity test using Antibody AT; curves (a) and (b) represent Peptide F and YAM Supernatant, respectively.

From these figures ATLA specificity of the antibody of the present invention can be seen.

While the invention has been described in detail and with reference to specific embodiments thereof, it will be apparent to one skilled in the art that various changes and modifications can be made therein without departing from the spirit and scope thereof.

What is claimed is:

1. An antibody specific for a human leukemia virus-related peptide obtained by collecting an antibody produced in a mammal by administering to the mammal an antigen prepared by reacting a human leukemia virus-related peptide selected from the group consisting of:

(a) a peptide represented by general formula (1):

H-Tyr-Val-Glu-Pro-Thr-Ala-Pro-Gln-Val-Leu-OH  (1)

(b) a peptide represented by general formula (2):

R-Ile-Pro-His-Pro-Lys-Asn-Ser-Ile-Gly-Gly-Glu-Val-OH  (2)

wherein R is a hydrogen atom or a group represented by the general formula H-Tyr;

(c) a peptide represented by general formula (3):

R-Thr-Trp-Thr-Pro-Lys-Asp-Lys-Thr-Lys-Val-Leu-OH  (3)

wherein R is the same as defined above;

(d) a peptide represented by general formula (4):

H-Val-Val-Gln-Pro-Lys-Lys-Pro-Pro-Pro-Tyr-OH  (4)

(e) a peptide represented by general formula (5):

R-Met-Gly-Gln-Ile-Phe-Ser-Arg-Ser-Ala-Ser-Pro-OH  (5)

wherein R is the same as defined above; and, (f) a peptide represented by general formula (6):

H-Tyr-Pro-Glu-Gly-Thr-Pro-Lys-Asp-Pro-Ile-Leu-Arg-Ser-Leu-OH  (6)

as a hapten, with a carrier in the presence of a hapten-carrier binding agent.

2. The antibody as claimed in claim 1, wherein said carrier is selected from the group consisting of an animal serum albumin, an animal serum globulin, an animal thyroglobulin, an animal hemoglobin, an animal hemocyanin, an ascaris extract, a polylysine, a polyglutamic acid, a lysine-glutamic acid copolymer, and a copolymer containing lysine or ornithine; and said hapten-carrier binding agent is selected from the group consisting of a diazonium compound, an aliphatic dialdehyde, a dimaleimide compound, a maleimidocarboxyl-N-hydroxysuccinimide ester and a carbodiimide.

3. The antibody as claimed in claim 2, wherein said mammal is rabbit or guinea pig.

4. The antibody as claimed in claim 3, wherein said carrier is an ascaris extract, Keyhole limpet hemocyanin or bovine serum albumin and said hapten-carrier binding agent is glutaraldehyde, N,N-dicyclohexylcarbodiimide or bisdiazotized benzidine.

5. A method for preparing an antibody of a human leukemia virus-related peptide comprising reacting a human leukemia virus-related peptide selected from the group consisting of:

(a) a peptide represented by general formula (1):

H-Tyr-Val-Glu-Pro-Thr-Ala-Pro-Gln-Val-Leu-OH     (1)

(b) a peptide represented by general formula (2):

R-Ile-Pro-His-Pro-Lys-Asn-Ser-Ile-Gly-Gly-Glu-Val-OH     (2)

wherein R is the same as defined above;

(c) a peptide represented by general formula (3):

R-Thr-Trp-Thr-Pro-Lys-Asp-Lys-Thr-Lys-Val-Leu-OH     (3)

wherein R is the same as defined above;

(d) a peptide represented by general formula (4):

H-Val-Val-Gln-Pro-Lys-Lys-Pro-Pro-Pro-Tyr-OH     (4)

(e) a peptide represented by general formula (5):

R-Met-Gly-Gln-Ile-Phe-Ser-Arg-Ser-Ala-Ser-Pro-OH     (5)

wherein R is the same as defined above; and, (f) a peptide represented by general formula (6):

H-Tyr-Pro-Glu-Gly-Thr-Pro-Lys-Asp-Pro-Ile-Leu-Arg-Ser-Leu-OH     (6)

as a hapten, with a carrier in the presence of a hapten-carrier binding agent to form an antigen, administering the resulting antigen to a mammal to form an antibody, and collecting the antibody.

* * * * *